United States Patent [19]
Pape et al.

[11] Patent Number: 5,182,156
[45] Date of Patent: Jan. 26, 1993

[54] COMPOSITE LAMINATE ADHESIVE TAPE COILED IN AN ENDLESS ROLL FORM AND PROCESS FOR FORMING THE LAMINATE ADHESIVE TAPE ROLL

[75] Inventors: Peter H. K. Pape, Hilden; Jorg O. P. Tuschy, Bedburg, both of Fed. Rep. of Germany

[73] Assignee: Minnesota Mining and Manufacturing Company, St. Paul, Minn.

[21] Appl. No.: 770,578

[22] Filed: Oct. 3, 1991

[30] Foreign Application Priority Data

Oct. 24, 1990 [DE] Fed. Rep. of Germany ....... 4033850

[51] Int. Cl.$^5$ ................................................ B32B 3/04
[52] U.S. Cl. .................................. 428/130; 428/352; 428/354; 428/906; 604/390; 604/370
[58] Field of Search .................. 428/354, 906, 130; 604/390, 370

[56] References Cited

U.S. PATENT DOCUMENTS

| | | | |
|---|---|---|---|
| 3,800,796 | 4/1974 | Jacob | 128/284 |
| 3,848,594 | 11/1974 | Buell | 604/390 |
| 3,893,460 | 7/1975 | Karami | 604/390 |
| 3,930,502 | 1/1976 | Tritsch | 128/287 |
| 3,987,793 | 10/1976 | Milnamow | 128/287 |
| 3,999,544 | 12/1976 | Feldman et al. | 128/284 |
| 4,005,712 | 2/1977 | Karami | 128/284 |
| 4,014,339 | 3/1977 | Tritsch | 128/287 |
| 4,020,842 | 5/1977 | Richman et al. | 128/287 |
| 4,029,098 | 6/1977 | Karami | 128/284 |
| 4,047,528 | 9/1977 | Karami | 128/287 |
| 4,047,529 | 9/1977 | Karami | 128/287 |
| 4,047,530 | 9/1977 | Karami | 128/287 |
| 4,051,853 | 10/1977 | Egan, Jr. | 128/287 |
| 4,058,125 | 11/1977 | Ness | 128/287 |
| 4,060,085 | 11/1977 | Karami | 128/287 |
| 4,066,081 | 1/1978 | Schaar | 128/287 |
| 4,074,716 | 2/1978 | Schaar | 128/287 |
| 4,168,196 | 9/1979 | Nemeth et al. | 156/184 |
| 4,227,530 | 10/1980 | Schatz | 128/287 |
| 4,237,890 | 12/1980 | Laplanche | 128/287 |
| 4,389,212 | 6/1983 | Tritsch | 604/389 |
| 4,516,976 | 5/1985 | Bell | 604/389 |
| 4,522,853 | 6/1985 | Szonn et al. | 428/40 |
| 4,552,560 | 11/1985 | Tritsch | 604/390 |
| 4,568,344 | 2/1986 | Suzuki et al. | 604/389 |
| 4,576,598 | 3/1986 | Tritsch | 604/390 |
| 4,576,600 | 3/1986 | Joa | 604/390 |
| 4,585,450 | 4/1986 | Rosch et al. | 604/390 |
| 4,643,729 | 2/1987 | Laplanche | 604/389 |
| 4,670,012 | 6/1987 | Johnson | 604/390 |
| 4,726,971 | 2/1988 | Pape et al. | 428/40 |
| 4,778,701 | 10/1988 | Pape et al. | 428/40 |
| 4,795,456 | 1/1989 | Borgers et al. | 604/390 |
| 4,801,480 | 1/1989 | Panza et al. | 428/354 |
| 4,917,928 | 4/1990 | Heinecke | 428/130 |
| 5,106,384 | 4/1992 | Polski | 604/390 |

FOREIGN PATENT DOCUMENTS

3440544-A1 7/1986 Fed. Rep. of Germany.
2206506A 11/1989 United Kingdom.

*Primary Examiner*—Jenna L. Davis
*Assistant Examiner*—B. Copenheaver
*Attorney, Agent, or Firm*—Gary L. Griswold; Roger R. Tamte; William J. Bond

[57] ABSTRACT

Composite laminated adhesive tape coiled endlessly in roll form, comprising a central tape and first and third fastening tapes each disposed at respective ends thereof, with the surface of said fastening tapes being provided, at least partly, with pressure-sensitive adhesive, wherein in cross section the composite laminated adhesive tape coiled endlessly in roll form is folded in Z-form, with the top, slanted and bottom bars of the Z-shape being formed by separate first, second and third tape sections of first fastening tape, second central tape and third fastening tape, respectively.

9 Claims, 2 Drawing Sheets

COMPOSITE LAMINATE ADHESIVE TAPE COILED IN AN ENDLESS ROLL FORM AND PROCESS FOR FORMING THE LAMINATE ADHESIVE TAPE ROLL

The invention relates to a composite laminated adhesive tape wound up to form an endless roll and to a process of forming the laminated adhesive tape roll.

A prior composite laminated adhesive tape wound up to form an endless roll (U.S. Pat. No. 4,778,701 (Pape, Tuschy) comprises a central elastomeric film having at least one extension axis transverse of the longitudinal direction of the film and first and second fastening tapes disposed above the elastomeric film. The two fastening tapes are adhered to the elastomeric film at their innermost ends and extend from the elastomeric film along said extension axis to non-adhering end portions. The undersides of the non-adhering end portions form an adhesive coated fastening surface. Below the elastomeric film and the fastening surface of the second fastening tape is provided a removable tape of which the top surface releasably contacts the fastening surface of the second fastening tape and whose underside is coated at least partly with an adhesive. Finally, there is provided below the removable tape a fastening film which adheres to a portion of the fastening surface of the first fastening strip and to a portion of the adhesive-coated side of the removable tape, which in the assembled laminated tape is secured in an area adjacent said elastomeric film. In the roll form of the composite laminate adhesive tape, the removable portion of the first fastening tape is adjacent that portion of the fastening surface of the first fastening tape which does not adhere to the fastening and elastomeric films. In this condition, the removable portion of the second fastening tape is adjacent that portion of the underside of the removable tape which does not adhere to the fastening film, and the fastening film is adjacent the upper surface of the elastomeric film, which lies between and is adhered to the end portions of the two fastening tapes.

From a roll of this laminated adhesive tape, which is relatively complex and wide in construction, narrow segments may be severed in a direction transverse to the wind-off direction of the roll of the laminated adhesive tape for use as adhesive diaper closure to be affixed to individual diapers.

There is also known a composite laminate adhesive tape coiled in roll form (U.S. Pat. No. 4,726,971 (Pape, Tuschy)) comprising a fastening tape divided into a firmly adhering portion and a fastening portion, a release tape and a connecting tape. The fastening tape comprises a suitable elongated backing of a material such as treated crepe paper, polymer film or the like, such material being provided with a suitable release coating to facilitate the withdrawal of the adhesive tape from the roll. One surface of the fastening tape is substantially coated with a normal pressure-sensitive adhesive, and approximately one third of that surface additionally has thereon a coating of an aggressive pressure-sensitive adhesive. This part of the surface of the fastening tape constitutes its firmly adhered part while the remainder of the surface forms the free fastening portion of the fastening tape. The connecting tape connects the inner end portion of the removable tape to the adjacent area of the fastening tape. A finger lift section is secured to the adhesive coating at the free end of the fastening portion of the fastening tape and projects from the fastening tape.

Individual adhesive tape closure for diapers may be severed from the roll of laminate adhesive tape transversely to its wind-off direction. Thereafter, the fastening and removable tapes are permanently affixed to opposite edge portions of a diaper wall, with the end of the fastening tape first lying over the removable tape in one edge area and then being withdrawn therefrom and secured to the opposite edge surface of the diaper wall.

Similar adhesive tape closure have been known to those skilled in the art.

A prior Z-folded adhesive tape closure (U.S. Pat. No. 4,237,890, FIGS. 3, 4 and 7) comprises a first tape section having a pressure-sensitive adhesive coating which terminates short of the fold in a second tape section, while the pressure-sensitive adhesive coating on a third tape section terminates short of a fold in that section. Separate lines of adhesive are provided for securing the fold of the second tape section to the first tape section, and the fold of the third tape section to the second tape section. In order to get the first tape section to separate from the second tape section when the closure is extended, the adhesive coating on the first tape section has thereon a layer of release coated paper which is connected to the second tape section via another line of adhesive. The paper layer continues to adhere to the closure after the diaper has been closed. The second and third tape sections are interconnected by another strip of adhesive which is broken when the closure is extended for closing the diaper.

The application of the multiple lines complicates the process of fabricating, and thus raises the cost of, the aforesaid prior diaper closure. From a practical viewpoint, it also is difficult to coil such diaper closure to form an endless roll since the web-like adhesive lines are likely to break. In addition, the liner held by the fourth web-like adhesive strip creates a process hazard in that, when being withdrawn from the roll, it may jam automatic machinery in which diaper closures are applied to diapers.

There is also known a commercially available Z-folded adhesive tape closure for disposable diapers (sold by Molnlycke) the fabrication of which involves the coating of an adhesive to the entire underside of a continuous backing and the application of a liner to a central portion and to the end of the backing in such a manner that, following the folding of the continuous coated backing into a Z-shape, the liner overlies all of the second portion of the Z-shape, the continuous adhesive coating on part of the fold between the second and the third tape portions and the adhesive-coated inner surface at the free end of the first tape section where it forms a finger lift. Because of the continuous adhesive coating and the liner needed for the central tape section, this prior adhesive tape closure requires a relatively great amount of material so that it is expensive; also, when machine-folded into a Z-configuration, the continuous adhesive coating on the one-piece backing frequently creates problems. Further, supply reels supporting corresponding Z-folded endless adhesive tape closures have a relatively great width, which has turned out to be a drawback when mounting the supply reel on a diaper machine and severing the individual adhesive tape closures from the supply roll mounted on the diaper machine.

In a similar adhesive tape closure (U.S. Pat. No. 4,576,598 (L. Tritsch)), an elongated backing has a pressure-sensitive adhesive applied to the entire top surface thereof to form a pressure-sensitive adhesive tape. The backing is a flexible material, such as a polyethylene or polypropylene film. At one end of the backing a release liner is applied to the pressure-sensitive adhesive coating, said liner consisting of paper or a plastic film having a suitable release coating on both sides and projecting from the end of the backing to form a movable finger lift. As a result, the releasable liner is affixed to the outer end of the pressure-sensitive adhesive tape in hinge fashion.

When providing the Tritsch Z-folded adhesive tape closure on a disposable diaper in a diaper machine, two stages of folding are involved. First, the releasable liner is secured to the pressuresensitive adhesive tape, which in turn is secured to the backing layer of the disposable diaper (FIG. 5). Thereafter, the adhesive tape and the releasable liner at its free outer end are folded into a Z-configuration, forming a first fold between the first and second tape sections and a second fold between the second central and third tape sections. The releasable liner is disposed between the second and third tape sections, and both its releasably coated surfaces engage the underside of the second tape section of the Z-shape on the one hand and the top surface of the third tape section of the Z-shape on the other. Thus, the second and third tape sections are held together while the liner section serving as finger lift projects from the Z-folded adhesive tape closure and may freely swing back and forth, creating a potential inconvenience (FIG. 4A). This prior adhesive tape closure also calls for relatively great amounts of material since the pressure-sensitive adhesive is coated on, and the liner applied to, the entire top surface. In addition, the freely movable projecting grip portion of the liner is felt to be nuisance in the process of applying the Z-folded adhesive tape closure to each diaper in automatic machinery.

In a prior multiply folded adhesive tape closure for disposable diapers according to U.S. Pat. No. 4,047,529 (Hamzeh Karami), the ends of a backing of the closure tape are provided with an adhesive on the underside thereof. After one adhesive-coated end of the backing has been attached to the diaper, the backing is folded to form a second section folded at a first fold line and a third section folded at a second fold line in such a manner that the third section—which also is the free adhesive-coated end of the backing—gets to lie adhesive coating at the initially free end of the backing engaging the surface opposite the adhesive coated side of the first backing end already attached to the diaper and so folding the latter in the folded condition (FIG. 4). In the process of fabricating this adhesive tape closure, the initially free adhesive coated end previously of the backing may be made to be shorter than the adhesive coated end previously attached to the diaper so that, following the folding and the attachment of the second backing end to the top surface of the first section, a portion extending inwardly from the second fold of the third section of the backing forms an adhesive-free grip portion which may be gripped by the user when the adhesive tape closure is unfolded for attaching the then free end of the backing to the diaper. In the fabrication in the form of endless supply reels of an adhesive tape closure multiply folded in this manner, the reels must be relatively wide, which may be a drawback when the rolls are to be mounted on a diaper machine. In addition, it is easy for the relatively wide tape rolls of the prior multiply folded adhesive tape closure to telescope to an unstable frustroconical shape, which creates additional problems when individual adhesive tape closures are to be served automatically from the roll.

There has also been known a multiply folded adhesive tape closure (U.S Pat. No. 4,670,012 (Johnson), FIGS. 4 to 9) the fabrication of which involves the folding of a closure tape made of a soft non-woven material into a harmonica pattern. The end section of the non-woven material is applied to the diaper with a tape having a relatively aggressive pressure-sensitive adhesive. A short outer end section of the non-woven material is attached to a second tape element having on its inner surface a less aggressive adhesion coating, the attachment being such that the second tape element has portions overlapping at both ends of the short end section. The end overlapping areas of the tape are secured either to adhesive-free areas of the non-woven material in its harmonica-folded condition or to the diaper. In comparison with a Z-fold, this multiple harmonica fold is relatively complicated; also, the additional tape element needed for attaching the adhesive tape closure to the diaper causes for increased material expense and prevents the closure tape from being coiled to form a supply roll.

Finally, there is also known a multiply folded adhesive tape closure (U.S. Pat. No. 4,014,339 (Tritsch), FIGS. 2, 3, 5 and 9 to 12) which consists of an elongated tape bent into a plurality of loop-shaped segments and of which the ends form fastening elements coated with a pressure-sensitive adhesive and adapted to be attached to opposite tags on a diaper. This patent is silent as to the coiling of such multiply folded adhesive tape closures in roll form.

It is the object of the invention to create a composite laminated adhesive tape coiled endlessly to form a roll which is easy to fabricate and may be provided in a reliable and relatively uncomplicated production process in the form of easily handled supply reels such that individual adhesive tape closures may be severed from the laminate adhesive tape roll without problems for attachment to diapers.

In accordance with the invention, there is provided an endlessly coiled composite laminate adhesive tape adapted to be made by a lamination process and consisting of separate tape sections or elements corresponding to the three bars of a Z-shape. The first and third sections are provided with a pressure-sensitive adhesive coating while the central or second tape section does not have such an adhesive coating.

In accordance with the invention, the laminated adhesive tape is laminated in a single trip without folding steps being necessary after the three tape sections have been interconnected. The second and third tape sections are turned over to form folds along two longitudinal edges before the three tapes are laminated. The inventive endlessly coiled laminated adhesive tape has a relatively narrow width so that supply rolls, particularly suited for mounting on diaper machines, may be obtained. It is possible in a particularly advantageous manner to coil the laminated tape into an endless roll of adhesive tape which is extremely stable on the supply reel as the folds can form raised portions along the longitudinal edges of the roll, on both sides, which in the coiling process generates a force perpendicular to the longitudinal edges.

The inventive laminated adhesive tape roll is easy and inexpensive to fabricate and raises no problems when used on a diaper machine.

An operator grips the free end of the first tape section of the adhesive tape closure severed from the laminated adhesive tape roll between two fingers and pulls it upwards. The first tape section preferably consists of an inexpensive dimensionally stable polymer film, paper or a non-woven sheet material treated on the outer surface thereof with a low-adhesion composition such as a silicone compound. The low-adhesion material should be compatible with the pressure-sensitive adhesive coating on the third tape section.

The laminated adhesive tape is formed of three tapes laminated together to correspond to the three tape sections, and the laminated adhesive tape is coiled up on a supply reel. In the coiling process, the low-adhesion material on the tape corresponding to the first tape section will contact the pressure-sensitive adhesive coating on the tape corresponding to the third tape section, thus acting as a separating or release layer between that adhesive coating and the tape corresponding to said first tape section.

The pressure-sensitive adhesive coating on the inner surface of the first tape section comprises an adhesive which on the one hand firmly adheres to the first tape section and on the other hand is adapted to be attached and re-attached to a diaper in a plurality of locations.

Preferably, the surface of the free end of the first tape section, which the user grips by his/her hands for pulling it up, may be free of adhesive. Alternatively, an adhesive coating on this end may be provided with a material which covers or masks the adhesive.

The adhesive on the first tape section is provided not only for attachment to a diaper but also for connecting the first tape section to the second tape section of the inventive laminate adhesive tape. As a result, no separate means has to be applied to the inventive laminated adhesive tape for interconnecting these two tape sections.

The second or central tape section of the inventive laminated adhesive tape preferably consists of an inexpensive polymer film, paper or non-woven sheet material. Also useful are materials which have elasticity so that the adhesive tape closure severed from the laminate adhesive tape roll has elastic properties, causing a better fit of the diaper it is used to close.

On the side facing the adhesive coating of the first tape section, the second tape section preferably is provided with a low-adhesion coating— such as a silicone compound—it preferably being needed only on those areas that contact adhesive layers in the laminate. The low-adhesion coating is compatible with the adhesive coating of the first tape section. Thus, there is not provided a separate layer to separate the second tape section, i.e., the side provided with the low-adhesion coating—from the adhesive coating on the first tape section. Instead, when the laminate adhesive tape is extended, the adhesive coating on the first tape section is released from the second tape section by virtue of the low-adhesion material on the second tape section. This low-adhesion material is applied prior to lamination.

The third tape section again preferably consists of an inexpensive dimensionally stable polymer film, paper or non-woven sheet material. It is provided on the side opposite the second tape section, i.e., its outer side, with a pressure-sensitive adhesive coating which is used to affix an adhesive tape closure severed from the Z-folded laminate coil to the diaper.

As in the first tape section, the pressure-sensitive adhesive coating on the third tape section serves not only to effect attachment to a diaper, but also to connect the second and third tape sections. As a result, the invention does without an additional line of adhesive for securing the second tape section to the third tape section.

Further, the third tape section may be provided with a coating of a low-adhesion material on its side facing the second tape section. This coating is not necessary for the finished laminate, rather, it is provided to enable a supply roll to be formed from which the tape forming the third tape section may be withdrawn in the lamination process.

The invention will now be explained in greater detail with reference to an embodiment example schematically shown in the drawings.

Figure 1:
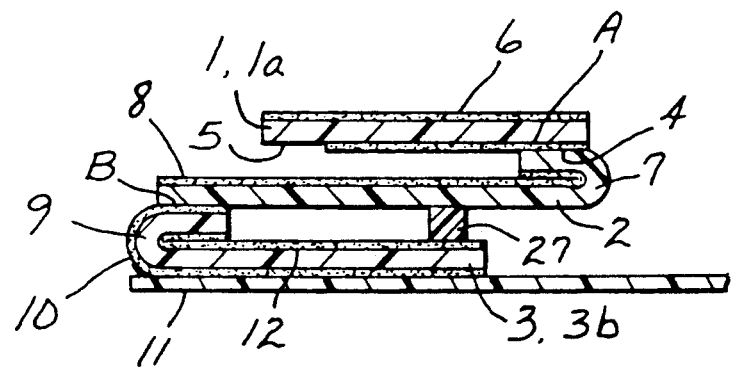
FIG. 1 shows a cross-sectional view of a Z-folded laminate adhesive tape.

As shown in FIG. 1, the Z-folded laminated adhesive tape (folded to a Z-configuration in cross section) consists of a first tape section 1 corresponding to the upper horizontal bar of the Z shape, a second tape section 2 corresponding to the slanted transverse bar of the Z, and a third tape section 3 corresponding to the lower horizontal bar of the Z shape.

First tape section 1 is provided at the side thereof facing second tape section 2 with a coating 4 of a pressure-sensitive adhesive. At its free end, first tape section 1 has an adhesive-free area 5, which on the adhesive tape closure, severed from the laminated adhesive tape roll, serves as a manual grip. On its outside, first tape section 1 is provided over its total length with a coating 6 of a low-adhesion material.

At one end, second or central tape section 2 is turned over towards first tape section 1 so that a fold 7 is formed. The end portion of the fold 7, which is not curved anymore, is preferably somewhat extended and provides a bonding surface A, to which adhesive coating 4 of the first tape section 1 adheres, see also FIG. 4. On the side facing first tape section 1, second tape section 2 has a coating 8 of a low-adhesion material thereon which extends over the entire length of second tape section 2, including the inner surface of fold 7.

The portion of pressure-sensitive adhesive layer 4, which overlaps with fold 7 bonding surface A, connects first tape section 1 (i.e., the end opposite its free end) to fold 7 of second tape section 2.

At one end, third tape section 3 is turned over toward second tape section 2 to form a fold 9. The end portion of the fold 9, which is not curved anymore, is preferably somewhat extended and provides the support for an adhesive bonding surface B, which is part of adhesive coating 10. On its side facing away from second tape section 2, third tape section 3 is provided with a coating 10 of a pressure-sensitive adhesive.

Adhesive coating 10 extends along the entire length of the third tape section 3, including the extended end portion of fold 9. The portion B of the pressure-sensitive adhesive layer 10 which is located at the extended end portion of fold 9 connects the end opposite fold 7 of second tape section 2 to fold 9 of third tape section 3.

As shown in FIG. 1, preferably there is provided a space between the end of the first tape section 1, which is not adhesively bonded to the fold 7 of the second tape section 2, and the turned end of fold 9 of the third tape section 3, on the one hand, as well as between the end of the third tape section 3 and the turned end of the fold 7 of the second tape section 2, on the other hand, so that there are always only three layers of material present across the entire width of the laminate adhesive tape. Consequently, the laminate adhesive tape has the same thickness on both sides thereof, so that the rolls coiled from the tape are stable.

The Z-folded laminated adhesive tape closure severed from the laminated adhesive tape roll is attached to the outside of the diaper along an edge 11 thereof by adhesive coating 10 on the side of third tape section 3 facing away from tape section 2. On its surface facing second tape section 2, including the engaging inner surfaces of fold 9, third tape section 3 has a coating 12 of a low-adhesion material.

Figure 2:
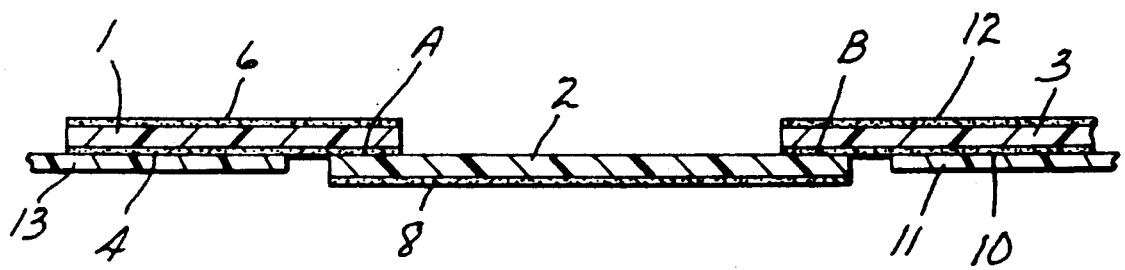
FIG. 2 shows a cross-sectional view through an adhesive tape closure of the kind depicted in FIG. 1 in a condition severed from the coiled laminated adhesive tape and extended for closing a diaper.

As shown in FIG. 2, after the adhesive tape closure severed from the laminate adhesive tape roll has been pulled apart to connect edge 11 of the diaper with opposite edge 13 on the outside of the diaper for closing same, pressure-sensitive adhesive coating 4 on first tape section 1 is connected with edge area 13 on the outside of the diaper.

Figure 3:
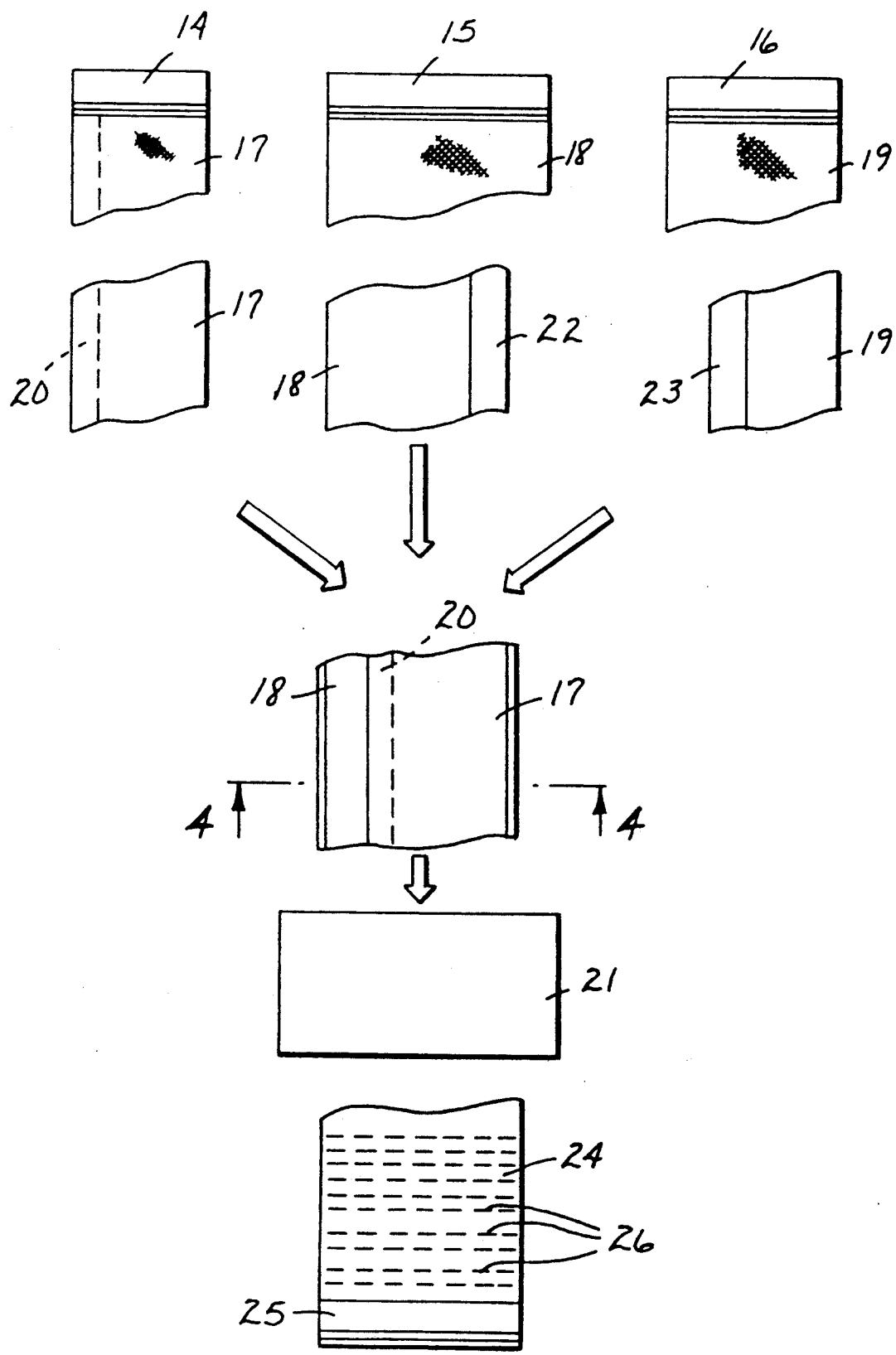
FIG. 3 shows a flow chart explaining the process of fabricating the laminated adhesive tape.

As shown in FIG. 3, three supply reels 14, 15 and 16 are provided for fabricating the laminated adhesive tape. Supply reel 14 has a first fastening tape 17 coiled thereon to form first tape section 1 of the laminated adhesive tape. Supply reel 15 has a length of second central tape 18 coiled thereon to form second tape section 2, and supply reel 16 has a third fastening tape 19 coiled thereon to form third tape section 3 of the laminated adhesive tape.

First fastening tape 17 is provided on its surface facing away from central tape 18 (see FIGS. 1 and 3) with a coating 6 of said low-adhesion material and on its side facing central tape 18 with pressure-sensitive adhesive layer 4. On the left hand side (in FIG. 3), a longitudinal line 20 (shown in phantom) is provided on the underside of first fastening tape 17, said line preferably being free of the pressure-sensitive adhesive coating 4 and forming adhesive-free area 5.

As shown in FIGS. 1 and 3, central tape 18 has on its surface facing first fastening tape 17 a coating 8 of said low-adhesion material, while third fastening tape 19 has on the side facing third fastening tape 19 said pressure-sensitive adhesive coating 10 and on its surface facing central tape 18 said coating 12 of the low-adhesion material which is capable with the pressure sensitive adhesive.

Tapes 17 to 19 are supplied to a laminating device 21. To this end, tapes 18 and 19 have one of their longitudinal edges turned up to form there along folds 22, 23 corresponding to folds 7 and 9 of second and third tape sections 2 and 3, respectively, of the laminated adhesive tape shown in FIG. 1.

Figure 4:
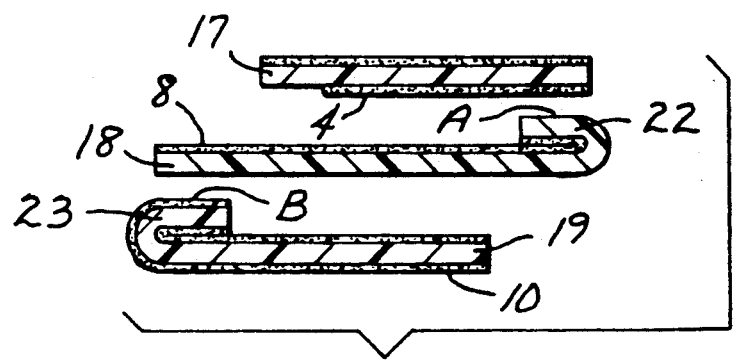
FIG. 4 shows an enlarged cross-sectional view taken along line 4—4 of FIG. 3.

As shown in FIG. 4, tapes 17, 18 and 19 are thereafter combined in a superimposed layered relationship as shown in FIG. 4, with adhesive coating 4 of first fastening tape 17 opposite tape 18 and adhesive coating 10 of second fastening 19 facing away from tape 18. Further, fold 22 of central tape 18 is aligned with one longitudinal edge of first fastening tape 17 and fold 23 of third fastening tape 19 with the longitudinal edge of central tape 18 opposite fold 22. The bonding and adhesive surfaces (A, B) mentioned above are located at folds 22 and 23 of the second and third fastening tapes 18, 19, respectively.

In this relationship, tapes 17 to 19 are laminated on top of each other in laminating machine 21. The laminated adhesive tape 24 issuing from laminating machine 21 is taken up on a roll of tape 25. Roll of tape 25 may then be transported to the diaper manufacturer where laminated adhesive tape 24 is withdrawn from the roll of tape and divided transversely into Z-folded adhesive tape closures, as shown by dashed line 26 in FIG. 3.

As shown in FIG. 1, a continuous or discontinuous strip 27 of a hot-melt adhesive or wax may be provided between the opposite surfaces of second and third tape sections 2 and 3 to hold the laminated adhesive tape in its folded condition until it is pulled apart by the user's fingers. As a consequence, strip 27 must be such as to break easily when the laminated adhesive tape is manually extended. The following examples are added to further explain the invention.

EXAMPLE 1

The first fastening tape comprises a polypropylene film 33 mm wide and 110/um thick coated on one side with a low-adhesion polyvinylsiloxane thermally curable to 100 % solids condition. The other side of the first fastening tape was coated with an adhesive comprising a synthetic rubber/resin blend of 37 parts by weight of a styrene-butadien-styrene triblock polymer (styrene-isoprene-styrene triblock, Kraton TM 1107), 48 parts by weight C-5 hydrocarbon resin (Escorez TM 1310) and 14 parts by weight poly-o-pinene resin (Arizona A25). At one side the film an area 5 mm wide was left free of the synthetic rubber/resin adhesive.

The central tape comprises a polyester film 44 mm wide and 40/um thick coated on one side with the same low-adhesion material (polyvinylsiloxane) as the first tape.

The third fastening tape comprises a biaxially oriented polypropylene film 35 mm wide and 40/um thick. The adhesive coated on this fastening tape almost corresponded to that on the first fastening tape and contained 34 parts by weight of rubber, 48.2 parts by weight of C-5 hydrocarbon resin and 16.8 parts by weight of poly-o-pinene resin. A low-adhesion polyurethane was coated on the other side of the third fastening tape.

One longitudinal edge of the central tape and of the third fastening tape were turned over to form a fold 5 mm wide before the tapes entered the laminating machine, this providing a connecting area 5 mm wide between the first and second tapes and between the second and third tapes, respectively. The finished laminated adhesive tape had a width of 39 mm. A laminated adhesive tape 400 m long was prepared with no difficulty. The laminated adhesive tape was divided transversely into strips 2.4-25 mm wide. Each adhesive tape closure had a length of 102 mm when pulled apart.

EXAMPLE 2

The first fastening tape consisted of polyethylene-coated paper 36 mm wide. The paper backing had a paper weight of 90 grams per sq.m and was coated with polyethylene in a coating weight of 18 grams per sq.m. The adhesive and silicone coatings were those of example 1. The finger lift was formed by masking a section 6 mm long of the pressure-sensitive adhesive coating with a polyester film 10/um thick.

The central tape was a paper having a paper weight of 90 grams per sq.m and silicone-coated on one side. The central tape was 45 mm wide. The first and third fastening tapes were affixed to the silicone-free side of the paper.

The third fastening tape was formed in the same way as the first fastening tape, but had a width of 36 mm and was not masked to provide a finger lift.

EXAMPLE 3

The first fastening tape comprised a white case polypropylene film having a "paper weight" of 90 grams per sq.m and coated on one side with the pressure-sensitive adhesive of example 1 and on the other side with low-adhesion silicone; its width was 32 mm. A finger lift was formed by leaving a strip 5 mm long uncoated with pressure-sensitive adhesive.

The central tape is formed by a white case polypropylene film having a "paper weight" of 79 grams per sq.m. silicone-coated on one side and 44 mm wide. The first and second fastening tapes were affixed to the silicone-free side of the central tape.

The third fastening tape was formed the same way as the first fastening tape with the exception that it did not have a finger lift and was 35 mm wide.

EXAMPLE 4

The first fastening tape was formed the same was as in example 3.

The central tape was a 40/um backing of biaxially oriented polypropylene (BOPP) 43 mm wide and coated with silicone on one side. The non-siliconized side of the central tape and indicia printed thereon. The first and third fastening tapes were affixed to the printed side.

The third fastening tape was a 40/um backing of biaxially oriented polypropylene (BOPP) as in the central tape, with one side of the backing coated with a synthetic pressure-sensitive rubber/resin adhesive as in claim 1. The other side of the backing was coated with a low-adhesion polyurethane formed by reacting polyvinylalcohol and an isocyanate. The width was 35 mm.

EXAMPLE 5

The first fastening tape was constructed the same way as in example 2.

The central tape consisted of a polyethylene-coated non-woven material, with the non-woven material and the polyethylene having a "paper weight" of 50 and 20 grams per sq.m., respectively. The polyethylene side of the central tape was coated with silicone.

The first and third fastening tapes were bonded to the non-woven side of the backing.

The third fastening tape was constructed as in example 2.

We claim:

1. Composite laminated adhesive tape coiled endlessly in roll form, comprising a central tape and first and second fastening tapes each disposed at opposite ends of the central tape, with the surfaces of said fastening tapes being provided at least partly with pressure-sensitive adhesive, the composite laminated adhesive tape coiled endlessly in roll form is folded in Z-form, with the top, slanted and bottom bars of the Z-shape being formed by separate first, second and third tape sections of first fastening tape, central tape or second fastening tape, respectively, the pressure-sensitive adhesive coatings are provided on the surface of the first fastening tape facing toward the central tape section and on the surface of second tape facing away from the central tape section, one end of the central tape and the opposite end of the second fastening tape are turned over toward the first tape section or the second tape section, respectively, to provide bonding and adhesive surfaces on folds to affix the first fastening tape, to the central tape, and the central tape to the second fastening tape, respectively, and the adhesive coating on the first fastening tape contacts said bonding surface at the fold of the central tape and the adhesive coating on the second fastening provides said adhesive surface at the fold of the second fastening tape.

2. The laminated adhesive tape of claim 1 wherein the first fastening tape has on its side facing away from the second tape section a low-adhesion coating, said coating compatible with the adhesive of the adhesive coating of second fastening tape.

3. The laminated adhesive tape of claim 1 wherein the first tape section has on the adhesive-coated surface an area which is adhesive-free or where the adhesive coating is masked.

4. The laminated adhesive tape of claim 1 wherein the central tape is provided on the side facing the first tape section with a low-adhesion material compatible with the adhesive coating on the first fastening tape.

5. The laminated adhesive tape of claim 1 wherein the side of the second fastening tape facing the second tape section is provided with a low-adhesion coating, said coating being compatible with the adhesive coating on the second fastening tape.

6. The laminated adhesive tape of claim 1 wherein the three tapes consist of a polymer film, paper or a non-woven sheet material.

7. The laminated adhesive tape of claim 1 wherein the central tape has elastic properties.

8. The laminated adhesive tape of claim 1 further comprising a hot-melt adhesive or wax being provided between the opposite surfaces of the second and third tape sections.

9. The laminated adhesive tape of claim 1 wherein a space is provided between the end of the first tape section, opposite the bonding end, and the turned end of the fold of the second fastening tape, as well as between the end of the third tape section, opposite the fold end, and the end of the fold of the second tape section, so that at any location across the entire width of the laminate adhesive tape only three overlapping layers of material are present.

* * * * *

UNITED STATES PATENT AND TRADEMARK OFFICE
CERTIFICATE OF CORRECTION

PATENT NO. : 5,182,156
DATED : January 26, 1993
INVENTOR(S) : Peter H.K. Pape and Jorg O.P. Tuschy It is certified that error appears in the above-identified patent and that said Letters Patent is hereby corrected as shown below:

Column 3, line 47, after the word "lie" and before the word "adhesive", insert --between the first and second sections, with the--.

Column 7, line 52, delete the word "capable" and insert therefor --compatible--.

Signed and Sealed this

Second Day of November, 1993

*Attest:*

BRUCE LEHMAN

*Attesting Officer*   Commissioner of Patents and Trademarks